US010092497B2

(12) United States Patent
Mueller et al.

(10) Patent No.: US 10,092,497 B2
(45) Date of Patent: Oct. 9, 2018

(54) BLEACHING AGENT CONTAINING POLYMERS

(71) Applicant: Henkel AG & Co. KGaA, Duesseldorf (DE)

(72) Inventors: Burkhard Mueller, Duesseldorf (DE); Udo Erkens, Neuss-Grimlinghausen (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/045,348

(22) Filed: Feb. 17, 2016

(65) Prior Publication Data

US 2016/0158142 A1 Jun. 9, 2016

Related U.S. Application Data

(63) Continuation of application No. PCT/DE2014/200328, filed on Jul. 17, 2014.

(30) Foreign Application Priority Data

Aug. 28, 2013 (DE) .................. 10 2013 217 206

(51) Int. Cl.
| | |
|---|---|
| *A61K 8/81* | (2006.01) |
| *A61K 8/92* | (2006.01) |
| *A61K 8/23* | (2006.01) |
| *A61Q 5/08* | (2006.01) |
| *A61K 8/90* | (2006.01) |

(52) U.S. Cl.
CPC .............. *A61K 8/8117* (2013.01); *A61K 8/23* (2013.01); *A61K 8/90* (2013.01); *A61K 8/92* (2013.01); *A61Q 5/08* (2013.01); *A61K 2800/882* (2013.01)

(58) Field of Classification Search
CPC .. A61Q 5/08; A61K 8/8117; A61K 2800/882; A61K 8/23; A61K 8/92; A61K 8/90
See application file for complete search history.

(56) References Cited

U.S. PATENT DOCUMENTS

| 6,365,136 B1 | 4/2002 | Lauscher et al. |
| 2003/0190297 A1 | 10/2003 | Narasimhan et al. |
| 2010/0170048 A1* | 7/2010 | Koike .................. A61K 8/23 |
| | | 8/407 |

FOREIGN PATENT DOCUMENTS

| EP | 0882444 A2 | | 12/1998 |
| EP | 1430875 A1 | | 6/2004 |
| EP | 1813259 A2 | | 8/2007 |
| FR | 2972637 | * | 9/2012 |
| WO | 2005/072689 A1 | | 8/2005 |
| WO | WO 2011/131676 | * | 10/2011 |
| WO | 2012/159929 A2 | | 11/2012 |

OTHER PUBLICATIONS

Legrand et al. EP 1430875, published: Jun. 23, 2004, Machine English translation obtained on Jun. 10, 2016.*
Simonet et al. FR 2972637, published: Sep. 21, 2012, Machine English translation obtained on Jun. 10, 2016.*
Truth in Aging, Hexyldecanol, published online on Jan. 25, 2013.*
PCT International Search Report (PCT/DE2014/200328) dated Oct. 15, 2014.

* cited by examiner

*Primary Examiner* — Johann R Richter
*Assistant Examiner* — Genevieve S Alley
(74) *Attorney, Agent, or Firm* — James C. Cummings

(57) ABSTRACT

An agent for lightening keratin fibers, which, with regard to its weight, includes 20 to 75 wt. % of oil(s), 0.05 to 5 wt. % of polymer(s) from the group of copolymers of ethylene/propylene/styrene and/or copolymers of butylene/ethylene/styrene, and/or copolymers of butylene/propylene/styrene, and 1 to 70 wt. % of peroxydisulfate(s), wherein the fibers contain 1 to 44 wt. % of potassium peroxydisulfate and 0 to <5 wt. % of sodium peroxydisulfate, and 0 to <5 wt. % of ammonium peroxydisulfate. The agent has increased storage stability, whereby not only the physical stability (settling, phase separation) but also the chemical stability (decomposition of the peroxide salts) is improved.

9 Claims, No Drawings

BLEACHING AGENT CONTAINING POLYMERS

FIELD OF THE INVENTION

The present invention generally relates to agents for oxidatively changing a color in the cosmetics field which are particularly suitable for lightening keratinic fibers, in particular human hair.

BACKGROUND OF THE INVENTION

The oxidizing agents present in blonding agents are capable of lightening the hair fiber by oxidatively destroying melanin, the hair's own pigment. For a moderate blonding effect, it is sufficient to use only hydrogen peroxide—optionally with the use of ammonia or other alkalizing agents—as the oxidizing agent; to achieve a stronger blonding effect, a mixture of hydrogen peroxide and peroxodisulfate salts and/or peroxomonosulfate salts is typically used.

For stability reasons, commercially available blonding agents are customarily offered in two preparations that are packaged separately from each other and mixed immediately before use to form a completely mixed application preparation. Commercially available blonding agents are usually composed of a liquid oxidizing agent preparation and a powder that contains solid oxidizing agents. As an alternative, it is possible to mix pasty agents with a liquid oxidizing agent preparation instead of the powder, whereby the dusting problem during production and mixing is avoided. Products comprising additional components are likewise offered commercially.

Pasty blonding agents generally contain larger amounts of an inert oil, which may result in stability problems (separation of the solid oxidizing agent from the oil). However, a concentration gradient may occur within the packaging even if peroxydisulfates have not fully settled, so that differing portions from the packaging may effectuate varying lightening after mixing. So as to minimize these problems, a high viscosity is desirable.

On the other hand, the viscosity of the blonding paste must be low enough for the paste to be easily and quickly mixed with the liquid oxidizing agent preparation. The resulting blonding mixture moreover must be sufficiently liquid so as to be applied easily and evenly, yet viscous enough so as not to drip off the head or application aids, such as brushes. In addition, the resulting blonding mixture should also not separate since consumers perceive settling or phase separation as a quality defect.

WO 2009/134875 A1 describes blonding agents containing persulfate salts and an oil gel, which, in turn, is composed of oil(s) and certain polymers.

According to this invention, stability against settling and phase separation are described as desirable properties of the agent.

EP 1 034 777 A1 discloses agents for lightening keratinic fibers, comprising at least two preparations (A) and (B) packaged separately from each other, which are mixed immediately before use to form an application mixture, wherein preparations (A) are oil-based and contain polymer(s) that form oleogels or lipogels.

It was the object of the present invention to further improve the properties of blonding agents, the goal being in particular to increase storage stability, wherein not only the physical stability (settling, phase separation), but also the chemical stability (decomposition of the persalts) were to be improved.

It has been shown that higher oil-containing blonding pastes thickened with specific polymers are particularly stable when the persulfates satisfy certain criteria.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An agent for lightening keratinic fibers includes, 20 to 75 wt. % oil(s); 0.05 to 5 wt. % polymer(s) from the group of the i. copolymers of ethylene/propylene/styrene, ii. copolymers of butylene/ethylene/styrene, iii. copolymers of butylene/propylene/styrene; and 1 to 70 wt. % peroxydisulfate(s), wherein the agent—based on the weight thereof—includes 1 to 44 wt. % potassium peroxydisulfate, 0 to <5 wt. % sodium peroxydisulfate, and 0 to <5 wt. % ammonium peroxydisulfate.

A method for changing the color of keratinic fibers in which at least two preparations (A) and (B) packaged separately from each other, of which preparation (A) contains at least one persulfate and preparation (B) contains at least one oxidizing agent, are mixed to form an application mixture, this mixture is applied to the fibers and rinsed off again after an exposure time, wherein preparation (A) comprises 0 to 75 wt. % oil(s); 0.05 to 5 wt. % polymer(s) from the group of the i. copolymers of ethylene/propylene/styrene, ii. copolymers of butylene/ethylene/styrene, iii. copolymers of butylene/propylene/styrene; 1 to 44 wt. % potassium peroxydisulfate; 0 to <5 wt. % sodium peroxydisulfate; and 0 to <5 wt. % ammonium peroxydisulfate.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In a first embodiment, it is an object of the present invention to provide agents for lightening keratinic fibers, containing, based on the weight of the agent,
  a) 20 to 75 wt. % oil(s);
  b) 0.05 to 5 wt. % polymer(s) from the group of the
    i. copolymers of ethylene/propylene/styrene,
    ii. copolymers of butylene/ethylene/styrene,
    iii. copolymers of butylene/propylene/styrene
  c) 1 to 70 wt. % peroxydisulfate(s);
characterized in that the agent—based on the weight thereof—comprises
  1 to 44 wt. % potassium peroxydisulfate,
  0 to <5 wt. % sodium peroxydisulfate, and
  0 to <5 wt. % ammonium peroxydisulfate.

Keratinic fibers, or also keratin fibers, shall be understood to mean furs, wool, feathers, and in particular human hair. Although the agents according to the invention are primarily suitable for lightening keratin fibers, in principle there are no objections to using them in other fields as well.

As the first ingredient, the agents according to the invention contain one or more oils. This oil is, or these oils are, preferably liquid under normal conditions.

A distinction is made between volatile and non-volatile oils in terms of the cosmetic oils. Non-volatile oils are understood to mean oils that have a vapor pressure of less than 2.66 Pa (0.02 mm Hg) at 20° C. and an ambient pressure of 1013 hPa. Volatile oils are understood to mean oils that have a vapor pressure of 2.66 Pa to 40000 Pa (0.02 to 300 mm Hg), preferably 10 to 12000 Pa (0.1 to 90 mm Hg), particularly preferably 13 to 3000 Pa, exceptionally preferably 15 to 500 Pa, at 20° C. and an ambient pressure of 1013 hPa.

Volatile cosmetic oils are usually selected from among the cyclic silicone oils having the INCI name Cyclomethicone. The INCI name Cyclomethicone shall be understood to mean in particular cyclotrisiloxane (hexamethyl cyclotrisiloxane), cyclotetrasiloxane (octamethyl cyclotetrasiloxane), cyclopentasiloxane (decamethyl cyclopentasiloxane) and cyclohexasiloxane (dodecamethyl cyclohexasiloxane). These oils have a vapor pressure of approximately 13 to 15 Pa at 20° C.

A preferred cyclomethicone substitute according to the invention is a mixture of $C_{13}$ to $C_{16}$ isoparaffins, $C_{12}$ to $C_{14}$ isoparaffins, and $C_{13}$ to $C_{15}$ alkanes, the viscosity of which at 25° C. is in a range of 2 to 6 mPas and which have a vapor pressure at 20° C. in the range of 10 to 150 Pa, preferably 100 to 150 Pa. Such a mixture is available, for example, under the designation SiClone SR-5 from Prespense Inc.

Further preferred volatile silicone oils are selected from volatile linear silicone oils, in particular volatile linear silicone oils having 2 to 10 siloxane units, such as hexamethyldisiloxane ($L_2$), octamethyltrisiloxane ($L_3$), decamethyltetrasiloxane ($L_4$), as they are present, for example, in the commercial products DC 2-1184, Dow Corning® 200 (0.65 cSt) and Dow Corning® 200 (1.5 cSt) from Dow Corning, and low molecular weight phenyl trimethicone having a vapor pressure at 20° C. of approximately 2000 Pa, as it is available from GE Bayer Silicones/Momentive, for example, under the name Baysilone Fluid PD 5.

Further preferred products according to the invention contain at least one volatile non-silicone oil. Preferred volatile non-silicone oils are selected from $C_8$ to $C_{16}$ isoparaffins, in particular from isononane, isodecane, isoundecane, isododecane, isotridecane, isotetradecane, isopentadecane, and isohexadecane, and mixtures thereof. Preferred are $C_{10}$ to $C_{13}$ isoparaffin mixtures, in particular those having a vapor pressure at 20° C. of 10 to 400 Pa, preferably 13 to 100 Pa.

Furthermore, particularly preferred cosmetic oils according to the invention are esters of the linear or branched, saturated or unsaturated fatty alcohols comprising 2 to 30 carbon atoms having linear or branched, saturated or unsaturated fatty acids containing 2 to 30 carbon atoms, which can be hydroxylated. Esters of the linear or branched saturated fatty alcohols comprising 2 to 5 carbon atoms having linear or branched, saturated or unsaturated fatty acids containing 10 to 18 carbon atoms, which can be hydroxylated, are preferred. Preferred examples in this regard are isopropyl palmitate, isopropyl stearate, isopropyl myristate, 2-hexyldecyl stearate, 2-hexyldecyl laurate, isodecyl neopentanoate, isononyl isononanoate, 2-ethylhexyl palmitate, and 2-ethylhexyl stearate. Likewise preferred are isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, ethylene glycol dipalmitate, n-hexyl laurate, n-decyl oleate, oleyl oleate, oleyl erucate, erucyl oleate, $C_{12-15}$ alkyl lactate, and di-$C_{12-13}$ alkyl malate, and the benzoic acid esters of linear or branched $C_{8-22}$ alkanols. Particularly preferred are benzoic acid-$C_{12-15}$-alkyl esters, for example available as the commercial product Finsolv® TN ($C_{12-15}$ alkyl benzoate), and benzoic acid isostearyl esters, for example available as Finsolv® SB, 2-ethylhexyl benzoate, for example available as Finsolv® EB, and benzoic acid-2-octyldodecyl ester, for example available as Finsolv® BOD.

The use of isopropyl esters of $C_{12}$ to $C_{18}$ carboxylic acids has proven to be particularly advantageous, in particular the use of isopropyl myristate, and particularly preferably mixtures of isopropyl myristate with $C_{10}$ to $C_{13}$ isoparaffin mixtures, the latter preferably having a vapor pressure at 20° C. of 10 Pa to 400 Pa.

A further particularly preferred ester oil is triethyl citrate. Further preferred products according to the invention contain triethyl citrate and at least one $C_8$ to $C_{16}$ isoparaffin, selected from isononane, isodecane, isoundecane, isododecane, isotridecane, isotetradecane, isopentadecane, and isohexadecane, and mixtures of these isoparaffins. Further preferred products according to the invention contain triethyl citrate and at least one $C_8$ to $C_{16}$ isoparaffin, selected from isononane, isodecane, isoundecane, isododecane, isotridecane, and mixtures of these $C_8$ to $C_{16}$ isoparaffins. Further preferred products according to the invention contain triethyl citrate and a mixture of isodecane, isoundecane, isododecane and isotridecane.

The expression "triglyceride" used hereafter shall be understood to mean "triesters of glycerol." Further preferred non-volatile oils according to the invention are selected from the triglycerides of linear or branched, saturated or unsaturated, optionally hydroxylated $C_8$ to $C_{30}$ fatty acids, provided these are liquid under normal conditions. The use of natural oils can be particularly suitable, such as soy bean oil, cottonseed oil, sunflower oil, palm oil, palm kernel oil, linseed oil, almond oil, castor oil, corn oil, rapeseed oil, olive oil, sesame oil, safflower oil, wheat germ oil, peach kernel oil, and the liquid components of coconut oil, and the like. Synthetic triglyceride oils are particularly preferred, in particular capric/caprylic triglycerides, such as the commercial products Myritol® 318 or Myritol® 331 (BASF/Cognis) comprising unbranched fatty acid esters and glyceryl triisostearol and glyceryl tri(2-ethylhexanoate) comprising branched fatty acid esters. Such triglyceride oils preferably account for a proportion of less than 50 wt. % of the total weight of all cosmetic oils in the product according to the invention.

Further particularly preferred non-volatile non-silicone oils according to the invention are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate.

Further particularly preferred non-volatile non-silicone oils according to the invention are selected from the symmetrical, asymmetrical or cyclic esters of carbonic acid comprising $C_6$ to $C_{20}$ alcohols, such as di-n-caprylyl carbonate (Cetiol® CC) or di-(2-ethylhexyl) carbonate (Tegosoft DEC). Esters of carbonic acid comprising $C_1$ to $C_5$ alcohols, such as glycerol carbonate or propylene carbonate, in contrast, are not compounds that are suitable as cosmetic oils.

Further oils that may be preferred according to the invention are selected from the esters of dimers of unsaturated $C_{12}$ to $C_{22}$ fatty acids (dimer fatty acids) comprising monohydric linear, branched or cyclic $C_2$ to $C_{18}$ alkanols or polyhydric linear or branched $C_2$ to $C_6$ alkanols. Particularly preferably, the total weight of dimer fatty acid esters is 0.5 to 10 wt. %, preferably 1 to 5 wt. %, in each case based on the weight of the total water-in-oil emulsion, without taking the weight of the blowing agent into consideration.

Further cosmetic oils that are particularly preferred according to the invention are selected from non-volatile silicone oils. Preferred non-volatile silicone oils according to the invention are selected from linear polyalkylsiloxanes having a kinematic viscosity at 25° C. of at least 5 cSt to 2000 cSt, in particular selected from linear polydimethylsiloxanes having a kinematic viscosity at 25° C. of 5 cSt to 2000 cSt, preferably 10 to 350 cSt, particularly preferably 50 to 100 cSt, as they are available, for example, under the trade name Dow Corning® 200 or Xiameter PMX from Dow Corning or Xiameter, respectively. Further preferred non-volatile silicone oils are phenyl trimethicone having a kinematic viscosity at 25° C. of 10 to 100 cSt, preferably of 15 to 30 cSt, and cetyl dimethicone.

Preferred agents according to the invention contain at least one non-volatile silicone oil, which is preferably selected from linear polyalkylsiloxanes having a kinematic viscosity at 25° C. of 5 cSt to 2000 cSt, preferably 10 to 350 cSt, particularly preferably 50 to 100 cSt, in particular selected from linear polydimethylsiloxanes having a kinematic viscosity at 25° C. of 5 cSt to 2000 cSt, preferably 10 to 350 cSt, particularly preferably 50 to 100 cSt, in a total amount of 0.1 to 30 wt. %, preferably 1 to 24 wt. %, particularly preferably 2 to 18 wt. %, exceptionally preferably 4 to 10 wt. %, in each case based on the weight of the total agent.

Several of the described oils have proven to be particularly suitable since they guarantee the physical and chemical stability of the blonding agent pastes over long periods of time and have excellent compatibility with the remaining ingredients according to the invention. Preferred agents according to the invention are characterized by comprising 22.5 to 70 wt. %, preferably 25 to 65 wt. %, more preferably 27.5 to 60 wt. %, particularly preferably 30 to 55 wt. %, and in particular 32.5 to 50 wt. % oil(s) from the group consisting of paraffin oil, polyisobutene, alkyl benzoates, isopropyl palmitate, isohexadecane, isododecane, isononyl isononanoate.

Further preferred agents according to the invention comprise 20 to 60 wt. %, preferably 22.5 to 55 wt. %, more preferably 25 to 50 wt. %, particularly preferably 27.5 to 45 wt. %, and in particular 30 to 40 wt. % paraffin oil.

The agents according to the invention contain 0.05 to 5 wt. % polymer(s) from the group of the copolymers of ethylene/propylene/styrene and/or of the copolymers of butylene/ethylene/styrene and/or of the copolymers of butylene/propylene/styrene as a further ingredient.

The described copolymers are preferably not copolymers in which the monomer units are statistically distributed, but block copolymers, particularly preferably diblock copolymers or triblock copolymers. Such block copolymers then comprise "hard" segments made of polystyrene and "soft" segments made of ethylene/propylene or ethylene/butylene or propylene/butylene. The individual blocks can comprise 10 to 10000, preferably 50 to 5000, and in particular 100 to 500 monomers. Preferred diblock copolymers are styrene-ethylene/propylene (S-EP) and styrene-ethylene/butylene (S-EB); preferred triblock copolymers are styrene-ethylene/propylene-styrene (S-EP-S) and styrene-ethylene/butylene-styrene (S-EB-S). It is particularly preferred according to the invention to use mixtures of diblock and triblock copolymers, wherein mixtures of styrene-ethylene/propylene (S-EP) and styrene-ethylene/propylene-styrene (S-EP-S) have been found to be particularly preferred. The proportion of diblock copolymers is especially particularly preferably 10 to 90 wt. %, and the proportion of triblock copolymers is 90 to 10 wt. %, in each case based on the weight of the polymer mixture.

Preferred agents according to the invention are characterized by comprising 0.1 to 4 wt. %, preferably 0.15 to 3 wt. %, more preferably 0.2 to 2.5 wt. %, particularly preferably 0.25 to 2 wt. %, more preferably 0.3 to 1.5 wt. %, and in particular 0.35 to 0.75 wt. % copolymers of ethylene/propylene/styrene.

Particularly preferred agents according to the invention are characterized by comprising 0.1 to 4 wt. %, preferably 0.15 to 3 wt. %, more preferably 0.2 to 2.5 wt. %, particularly preferably 0.25 to 2 wt. %, more preferably 0.3 to 1.5 wt. %, and in particular 0.35 to 0.75 wt. % diblock copolymers of ethylene/propylene/styrene (S-EP).

Likewise particularly preferred agents according to the invention are characterized by comprising 0.1 to 4 wt. %, preferably 0.15 to 3 wt. %, more preferably 0.2 to 2.5 wt. %, particularly preferably 0.25 to 2 wt. %, more preferably 0.3 to 1.5 wt. %, and in particular 0.35 to 0.75 wt. % triblock copolymers of ethylene/propylene/styrene (S-EP-S).

Particularly preferred diblock copolymers of ethylene/propylene/styrene (S-EP) can be described by the formula (I)

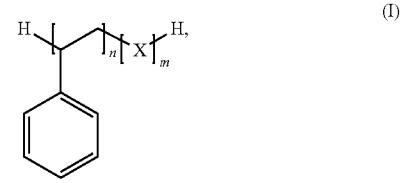

in which —$[X]_n$— denotes a block comprising ethylene and propylene monomer units, which may be present in the form of a block or statistically distributed, where m denotes a number from 10 to 10000, preferably from 50 to 5000, and in particular from 100 to 500 and relates to the total number of ethylene and propylene monomer units in the block, and n denotes a number from 10 to 10000, preferably from 50 to 5000, and in particular from 100 to 500.

Particularly preferred triblock copolymers of ethylene/propylene/styrene (S-EP) can be described by the formula (II)

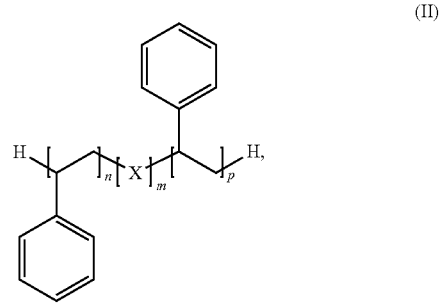

in which —[X]$_m$— denotes a block comprising ethylene and propylene monomer units, which may be present in the form of a block or statistically distributed, where m denotes a number from 10 to 10000, preferably from 50 to 5000, and in particular from 100 to 500 and relates to the total number of ethylene and propylene monomer units in the block, and n and p, independently of one another, denote a number from 10 to 10000, preferably from 50 to 5000, and in particular from 100 to 500.

Preferred agents according to the invention are characterized by comprising 0.1 to 4 wt. %, preferably 0.15 to 3 wt. %, more preferably 0.2 to 2.5 wt. %, particularly preferably 0.25 to 2 wt. %, more preferably 0.3 to 1.5 wt. %, and in particular 0.35 to 0.75 wt. % copolymers of butylene/ethylene/styrene.

Likewise particularly preferred agents according to the invention are characterized by comprising 0.1 to 4 wt. %, preferably 0.15 to 3 wt. %, more preferably 0.2 to 2.5 wt. %, particularly preferably 0.25 to 2 wt. %, more preferably 0.3 to 1.5 wt. %, and in particular 0.35 to 0.75 wt. % diblock copolymers of butylene/ethylene/styrene (S-EB).

Likewise particularly preferred agents according to the invention are characterized by comprising 0.1 to 4 wt. %, preferably 0.15 to 3 wt. %, more preferably 0.2 to 2.5 wt. %, particularly preferably 0.25 to 2 wt. %, more preferably 0.3 to 1.5 wt. %, and in particular 0.35 to 0.75 wt. % triblock copolymers of butylene/ethylene/styrene (S-EB-S).

Particularly preferred diblock copolymers of butylene/ethylene/styrene (S-EB) can be described by the formula (III)

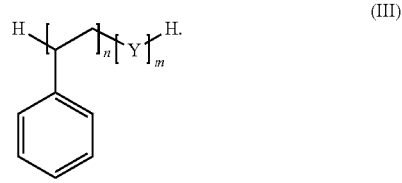

(III)

in which —[Y]$_m$— denotes a block comprising ethylene and butylene monomer units, which may be present in the form of a block or statistically distributed, where m denotes a number from 10 to 10000, preferably from 50 to 5000, and in particular from 100 to 500 and relates to the total number of ethylene and butylene monomer units in the block, and n denotes a number from 10 to 10000, preferably from 50 to 5000, and in particular from 100 to 500.

Particularly preferred triblock copolymers of butylene/ethylene/styrene (S-EB-S) can be described by the formula (IV)

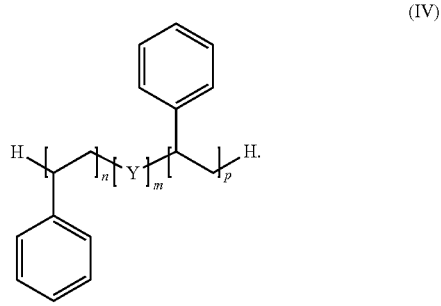

(IV)

in which —[Y]$_m$— denotes a block comprising ethylene and butylene monomer units, which may be present in the form of a block or statistically distributed, where m denotes a number from 10 to 10000, preferably from 50 to 5000, and in particular from 100 to 500 and relates to the total number of ethylene and butylene monomer units in the block, and n and p, independently of one another, denote a number from 10 to 10000, preferably from 50 to 5000, and in particular from 100 to 500.

The preparations according to the invention contain 1 to 70 wt. % peroxydisulfate(s) as a further essential ingredient, wherein the agent, based on the weight thereof, contains 1 to 44 wt. % potassium peroxydisulfate and 0 to <5 wt. % sodium peroxydisulfate and 0 to <5 wt. % ammonium peroxydisulfate.

In a preferred embodiment of the present invention, the agent according to the invention comprises 5 to 43.5 wt. %, preferably 10 to 43 wt. %, more preferably 15 to 42.5 wt. %, particularly preferably 20 to 42 wt. %, and in particular 30 to 41 wt. % potassium peroxydisulfate.

It is extremely preferable to always keep the amount of potassium peroxydisulfate considerably greater than the amount of sodium and ammonium peroxydisulfate that may be used. It has been shown that the chemical and physical stability of the agents according to the invention rises as the proportion of potassium peroxydisulfate in the total amount of peroxydisulfates increases. In preferred agents, the weight ratio of potassium peroxydisulfate to sodium and ammonium peroxydisulfate is thus >2, preferably >5, more preferably >10, still more preferably >15, and in particular >20. This weight ratio is ascertained by dividing the wt. % amount of potassium peroxydisulfate by the sum of the wt. % amount of sodium and ammonium peroxydisulfate.

Preferred agents according to the invention are characterized in that the weight ratio of potassium peroxydisulfate present in the agent to sodium and ammonium peroxydisulfates present in the agent is >10:1, preferably >12.5:1, more preferably >15:1, particularly preferably >17.5:1, and in particular >20:1.

Extremely preferred agents according to the invention comprise 0 to <2.5 wt. %, preferably 0 to <1 wt. %, more preferably 0 to <0.5 wt. %, particularly preferably 0 to <0.1 wt. %, and in particular 0 wt. % peroxydisulfates from the group of sodium peroxydisulfate and/or ammonium peroxydisulfate.

The agents according to the invention may contain at least one natural polymer as a further ingredient. Cellulose derivatives that are utilized as thickening agents can be used, for example, as the natural polymer. Examples are agar-agar, carrageenan, alginates, xanthan gum, karaya gum, ghatti gum, tragacanth, scleroglucan gums or gum arabic, alginates, pectins, polyoses, guar gums, carob seed powder, linseed gums, dextrans, pectins, starch fractions and derivatives such as amylose, amylopectin, and dextrins, gelatins, and casein, as well as cellulose derivatives such as methyl cellulose, carboxyalkyl celluloses such as carboxymethyl cellulose, and hydroxyalkyl celluloses such as hydroxyethyl cellulose.

Natural polymers from the described substance classes are commercially available and are offered, for example, under the trade names Deuteron®-XG (anionic heteropolysaccharide based on β-D-glucose, D-manose, D-glucuronic acid, Schoener GmbH), Deuteron®-XN (nonionogenic polysaccharide, Schoener GmbH), Protanal RF 6650 alginate (sodium alginate, FMC Biopolymer), Cekol (cellulose gum, Kelco), Kelzan (xanthan gum biopolymer, Kelco), Xanthan FN (xanthan gum biopolymer, Jungbunzlauer), Keltrol, for example Keltrol CG-T (xanthan gum biopolymer, Kelco) or Keltrol CG-SFT (xanthan gum biopolymer, Kelco).

In a preferred embodiment of the invention, the agents according to the invention contain xanthan gum. Preferred xanthan gums according to the invention are those that yield transparent preparations after swelling. Use of the xanthan gum biopolymer is particularly preferred, which is marketed under the trade name Keltrol CG-SFT by Kelco.

In a preferred embodiment, an agent according to the invention comprises 0.1 to 5 wt. %, preferably 0.5 to 4 wt. %, more preferably 1 to 3 wt. %, particularly preferably 1.25 to 2.5 wt. %, and in particular 1.5 to 2 wt. % xanthan gum.

Stabilizers that the agents according to the invention contain can preferably be long chain fatty alcohols, which are preferably selected from the group consisting of arachyl alcohol (eicosan-1-ol), gadoleyl alcohol ((9Z)-eicos-9-en-1-ol), arachidyl alcohol ((5Z,8Z,11Z,14Z)-eicosa-5,8,11,14-tetraen-1-ol), heneicosyl alcohol, (heneicosan-1-ol), behenyl alcohol (docosan-1-ol), erucyl alcohol ((13Z)-docos-13-en-1-ol), and brassidyl alcohol ((13E)-docosen-1-ol).

These long chain fatty alcohols have a chain length of at least 20 carbon atoms. Within this group, specific long chain fatty alcohols have proven to be especially particularly suitable.

In one particularly preferred embodiment, an agent for blonding and/or bleaching keratinic fibers is characterized by comprising arachyl alcohol (eicosan-1-ol).

In a further particularly preferred embodiment, an agent for blonding and/or bleaching keratinic fibers is characterized by comprising behenyl alcohol (docosan-1-ol).

In a further particularly preferred embodiment, an agent for blonding and/or bleaching keratinic fibers is characterized by comprising arachyl alcohol (eicosan-1-ol) and/or behenyl alcohol (docosan-1-ol).

Furthermore, it has been found that it is advantageous if the long chain fatty alcohols, in particular arachyl alcohol (eicosan-1-ol) and/or behenyl alcohol (docosan-1-ol), are present in certain quantity ranges in the agent according to the invention. Preferred agents according to the invention contain one or more long chain fatty alcohols (a) from the group consisting of arachyl alcohol (eicosan-1-ol), gadoleyl alcohol ((9Z)-eicos-9-en-1-ol), arachidyl alcohol ((5Z,8Z,11Z,14Z)-eicosa-5,8,11,14-tetraen-1-ol), heneicosyl alcohol, (heneicosan-1-ol), behenyl alcohol (docosan-1-ol), erucyl alcohol ((13Z)-docos-13-en-1-ol), and brassidyl alcohol ((13E)-docosen-1-ol) in a total amount of 0.3 to 3.4 wt. %, preferably 0.4 to 2.6 wt. %, more preferably 0.5 to 1.8 wt. %, and particularly preferably 0.6 to 0.9 wt. %, based on the total weight of the ready-to-use agent.

In an especially particularly preferred embodiment, an agent according to the invention is characterized by comprising, as fatty alcohol(s), arachyl alcohol (eicosan-1-ol) and/or behenyl alcohol (docosan-1-ol) in a total amount of 0.3 to 3.4 wt. %, preferably 0.4 to 2.6 wt. %, more preferably 0.5 to 1.8 wt. %, and particularly preferably 0.6 to 0.9 wt. %, based on the total weight of the ready-to-use agent.

In addition to the specific long chain fatty alcohols having a chain length of at least 20 carbon atoms, the agent according to the invention may additionally contain further, shorter chain fatty alcohols having a chain length of 12 to 18 carbon atoms. Suitable shorter chain fatty alcohols having a saturated $C_{12}$ to $C_{18}$ alkyl chain are, for example, dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol) and octadecan-1-ol (octadecyl alcohol, stearyl alcohol). A suitable shorter chain fatty alcohol having an unsaturated $C_{12}$ to $C_{18}$ alkyl chain is (9Z)-octadec-9-en-1-ol (oleyl alcohol), for example.

The use of branched longer chain alcohols having a chain length of 12 to 18 carbon atoms is especially particularly preferred with respect to the consistency and ability to apply the products according to the invention, wherein hexyldecanol has proven to be particularly suitable. Particularly preferred agents according to the invention are characterized by comprising, based on the weight thereof, 2 to 10 wt. %, more preferably 3.5 to 8 wt. %, particularly preferably 4 to 7 wt. %, and in particular 5 to 6.5 wt. % branched longer chain alcohols having a chain length of 12 to 18 carbon atoms, preferably 2-hexyldecan-1-ol.

Cetyl stearyl alcohol is particularly suitable for physical and chemical stabilization. In this regard, preferred agents according to the invention are those comprising 1 to 15 wt. %, preferably 2 to 10 wt. %, more preferably 3.5 to 8 wt. %, particularly preferably 4 to 7 wt. %, and in particular 5 to 6.5 wt. % cetearyl alcohol.

The blonding agents may moreover contain alkalizing agents. Preferred alkalizing agents are, for example, ammonia, alkanolamines, basic amino acids, and inorganic alkalizing agents such as alkali metal and alkaline earth metal hydroxides, alkali metal and alkaline earth metal metasilicates, alkali metal and alkaline earth metal phosphates, and alkali metal and alkaline earth metal hydrogen phosphates. Preferred metal ions are lithium, sodium and/or potassium. Ammonia is a particularly preferred alkalizing agent.

Inorganic alkalizing agents that can be used according to the invention are preferably selected from sodium hydroxide, potassium hydroxide, calcium hydroxide, barium hydroxide, sodium phosphate, potassium phosphate, sodium silicate, potassium silicate, magnesium silicate, sodium carbonate and potassium carbonate. Sodium hydroxide and/or potassium hydroxide are particularly preferred.

It has been found to be preferred to use metasilicates in the compositions according to the invention. These increase the bleaching action, while also reducing damage to the keratinic fiber. Preferably alkali metal and alkaline earth metal metasilicates, particularly preferably alkali metal metasilicates, and in particular sodium metasilicates have proven to be suitable. Preferred agents according to the invention thus comprise, based on the weight thereof, 5 to <10 wt. %, preferably 6 to <9.5 wt. %, more preferably 6.5 to <9 wt. %, particularly preferably 7 to <8.5 wt. %, and in particular 7.5 to <8 wt. % alkali metal and alkaline earth metal metasilicates, preferably alkali metal metasilicates, and in particular sodium metasilicates.

Alkalizing agents that can be used according to the invention are preferably selected from alkanolamines composed of primary, secondary or tertiary amines having a $C_2$-$C_6$ alkyl basic structure, which carries at least one hydroxyl group. Particularly preferred alkanolamines are selected from the group consisting of 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methyl-propanol, 2-amino-2-methylbutanol, 3-amino-2-methylpropan-1-ol, 1-amino-2-methylpropan-2-ol, 3-aminopropan-1,2-diol, 2-amino-2-methylpropan-1,3-diol, 2-amino-2-ethyl-1,3-propane diol, N,N-dimethyl-ethanolamine, methylglucamine, triethanolamine, diethanolamine and triisopropanolamine. Particularly preferred alkanolamines are monoethanolamine, 2-amino-2-methylpropanol and triethanolamine.

The basic amino acids that can be used as the alkalizing agent according to the invention are preferably selected from the group consisting of L-arginine, D-arginine, D/L-arginine, L-lysine, D-lysine, D/L-lysine, L-ornithine, D-ornithine, D/L-ornithine, L-histidine, D-histidine and/or D/L-histidine. L-arginine, D-arginine and/or D/L-arginine are particularly preferred as an alkalizing agent within the meaning of the invention.

Some consumers find the intense odor development of ammonia to be bothersome or annoying. While ammonia is a preferred alkalizing agent, ready-to-use preparations that are free of ammonia may thus be preferred according to the invention. Preferred alkalizing agents for preparations that are free of ammonia are monoethanolamine, 2-amino-2-methyl-propanol and triethanolamine.

If the ready-to-use mixtures contain alkalizing agents, preferred preparations according to the invention are those containing alkalizing agents in an amount from 0.05 to 20 wt. %, in particular from 0.5 to 10 wt. %, in each case based on the total weight of the ready-to-use agent.

The compositions according to the invention can additionally contain at least one further bleach booster that is different from the inorganic persalts.

Compounds that, under perhydrolysis conditions, yield aliphatic peroxocarboxylic acids having preferably 1 to 10 carbon atoms, in particular 2 to 4 carbon atoms, and/or optionally substituted perbenzoic acid, can be used as bleach boosters. Suitable substances are those that carry 0- and/or N-acyl groups having the described carbon atomic number and/or optionally substituted benzoyl groups. Polyacylated alkylenediamines, in particular tetra acetyl ethylene diamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or iso-nonanoyl oxybenzene sulfonate (n- or iso-NOBS), carboxylic acid anhydrides, in particular phthalic anhydride, acylated polyhydric alcohols, in particular triacetin, ethylene glycol diacetate and 2,5-diacetoxy-2,5-dihydrofuran are preferred.

A second object of the invention is to provide a method for changing the color of keratinic fibers, in which at least two preparations (A) and (B) packaged separately from each other, of which preparation (A) contains at least one persulfate and preparation (B) contains at least one oxidizing agent, are mixed to form an application mixture, this mixture is applied to the fibers and rinsed off again after an exposure time, characterized in that preparation (A) comprises
  a) 20 to 75 wt. % oil(s);
  b) 0.05 to 5 wt. % polymer(s) from the group of the
    i. copolymers of ethylene/propylene/styrene,
    ii. copolymers of butylene/ethylene/styrene,
    iii. copolymers of butylene/propylene/styrene
  c) 1 to 44 wt. % potassium peroxydisulfate,
  d) 0 to <5 wt. % sodium peroxydisulfate, and
  e) 0 to <5 wt. % ammonium peroxydisulfate.

The ready-to-use agents are prepared immediately before use on the hair by mixing the two preparations (A) and (B) and optionally a third preparation (C) and/or further preparations. In ready-to-use agents that are mixed from more than two preparations to form a completely mixed application mixture, it may be immaterial whether initially two preparations are mixed together and subsequently the third preparation is added and mixed in, or whether all preparations are combined at once and subsequently mixed. Mixing can be carried out by stirring in a bowl or a cup or by shaking in a closable container.

The term "immediately" shall be understood to mean a time period from a few seconds to one hour, preferably up to 30 min, in particular up to 15 min.

The agents according to the invention are used in a method for lightening keratinic fibers, in particular human hair, in which the agent is applied to the keratin-containing fibers, allowed to remain on the fibers at a temperature from room temperature to 45° C. for an exposure duration of 10 to 60 minutes, and subsequently rinsed off again using water or washed off using a shampoo.

The exposure time of the ready-to-use lightening agents is preferably 10 to 60 min, in particular 15 to 50 min, particularly preferably 20 to 45 min. During the exposure time of the agent on the fiber, it may be advantageous to support the lightening process by supplying heat. The heat can be supplied by an external heat source, such as by way of a hot air blower, or by the body temperature of the subject, in particular when the hair of a living subject is lightened. If the latter option applies, the section to be lightened is usually covered with a cap. An exposure phase at room temperature is likewise covered by the invention. The temperature is preferably between 20° C. and 40° C., in particular between 25° C. and 38° C., during the exposure time. The lightening agents already yield good blonding and lightening results at physiologically compatible temperatures of less than 45° C.

After the exposure time has ended, the remaining lightening preparation is rinsed off the hair using water or a cleaning agent. In particular commercially available shampoo may be used as the cleaning agent, wherein the cleaning agent can be dispensed with and the rinsing process can be carried out using tap water in particular when the lightening agent includes a strong surfactant-containing carrier.

The preferred embodiments of the first subject matter of the invention apply, mutatis mutandis, also to the second subject matter of the invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for lightening keratinic fibers, including, based on the weight of the agent,
  a) 20 to 75 wt. % oil(s);
  b) 0.05 to 5 wt. % copolymers of butylene/propylene/styrene;
  c) 1 to 70 wt. % peroxydisulfate(s);
  (d) 2 to 10 wt. % 2-hexyldecan-1-ol;
  (e) 3.5 to 8 wt. % cetearyl alcohol; and
  (f) 0.6 to 0.9 wt. % arachyl alcohol (eicosan-1-ol);
  wherein the agent includes
    1 to 44 wt. % potassium peroxydisulfate,
    0 to <5 wt. % sodium peroxydisulfate, and
    0 to <5 wt. % ammonium peroxydisulfate.

2. The agent according to claim 1, including 22.5 to 70 wt. % of the oil(s), such oil(s) selected from the group consisting of paraffin oil, polyisobutene, alkyl benzoates, isopropyl palmitate, isohexadecane, isododecane, and isononyl isononanoate.

3. The agent according to claim 1, wherein the oil(s) include 20 to 60 wt. % paraffin oil based on the weight of the agent.

4. The agent according to claim 1, wherein the potassium peroxydisulfate is included at a concentration of 30 to 41 wt. %.

5. The agent according to claim 1, including 0 to <2.5 wt. % of one or both of the peroxydisulfates from the group consisting of sodium peroxydisulfate and ammonium peroxydisulfate.

6. The agent according to claim 5, wherein a weight ratio of potassium peroxydisulfate present in the agent to sodium and ammonium peroxydisulfates present in the agent is >10:1.

7. The agent according to claim 1, further including 0.1 to 5 wt. % xanthan gum.

8. The agent according to claim 1, further including, based on the weight thereof, 5 to <10 wt. % alkali metal and alkaline earth metal metasilicates.

9. A method for changing the color of keratinic fibers, including mixing at least two preparations (A) and (B) packaged separately from each other, of which preparation (A) contains at least one persulfate and preparation (B) contains at least one oxidizing agent, to form an application mixture, and applying the mixture to the fibers and rinsing the mixture off again after an exposure time, wherein the preparation (A) includes
   a) 0 to 75 wt. % oil(s);
   b) 0.05 to 5 wt. % copolymers of butylene/propylene/styrene;
   c) 1 to 44 wt. % potassium peroxydisulfate;
   d) 0 to <5 wt. % sodium peroxydisulfate;
   e) 0 to <5 wt. % ammonium peroxydisulfate;
   f) 2 to 10 wt. % 2-hexyldecan-1-ol;
   g) 3.5 to 8 wt. % cetearyl alcohol; and
   h) 0.6 to 0.9 wt. % arachyl alcohol (eicosan-1-ol).

* * * * *